(12) United States Patent
Joshi

(10) Patent No.: US 8,410,052 B2
(45) Date of Patent: *Apr. 2, 2013

(54) ORAL ADMINISTRATION OF A CALCITONIN

(75) Inventor: Yatindra Joshi, Princeton, NJ (US)

(73) Assignee: Novartis AG, Basel (CH)

( * ) Notice: Subject to any disclaimer, the term of this patent is extended or adjusted under 35 U.S.C. 154(b) by 360 days.

This patent is subject to a terminal disclaimer.

(21) Appl. No.: 12/529,371

(22) PCT Filed: Feb. 29, 2008

(86) PCT No.: PCT/US2008/055399
§ 371 (c)(1),
(2), (4) Date: Sep. 1, 2009

(87) PCT Pub. No.: WO2008/109385
PCT Pub. Date: Sep. 12, 2008

(65) Prior Publication Data
US 2010/0210526 A1   Aug. 19, 2010

Related U.S. Application Data

(60) Provisional application No. 60/892,594, filed on Mar. 2, 2007.

(51) Int. Cl.
*A61K 38/23* (2006.01)
*A61K 31/195* (2006.01)
*C07C 229/00* (2006.01)
*C07K 14/585* (2006.01)

(52) U.S. Cl. .......... 514/11.9; 514/16.8; 514/16.9; 514/563; 530/307; 562/444; 562/450

(58) Field of Classification Search .......... None
See application file for complete search history.

(56) References Cited

U.S. PATENT DOCUMENTS

| 5,629,020 | A | 5/1997 | Leone-Bay et al. |
| 7,049,283 | B2 | 5/2006 | Ault et al. |
| 7,569,539 | B2 * | 8/2009 | Azria et al. ............ 514/1.1 |
| 7,749,954 | B2 * | 7/2010 | Azria et al. ............ 514/11.9 |
| 2002/0065255 | A1 | 5/2002 | Bay et al. |
| 2002/0123459 | A1 | 9/2002 | Ault et al. |
| 2005/0054557 | A1 | 3/2005 | Goldberg |
| 2006/0135402 | A1 * | 6/2006 | Azria et al. ............ 514/2 |
| 2006/0194722 | A1 * | 8/2006 | Azria et al. ............ 514/12 |

FOREIGN PATENT DOCUMENTS

| WO | 00/59480 | 10/2000 |
| WO | 00/59863 | 10/2000 |
| WO | 02/45754 | 6/2002 |
| WO | 03/015822 | 2/2003 |
| WO | 2004/012772 | 2/2004 |
| WO | WO 2004012772 A1 * | 2/2004 |
| WO | 2005/014031 | 2/2005 |
| WO | WO 2005014031 A1 * | 2/2005 |

OTHER PUBLICATIONS

Lee YH, Sinko PJ. Oral delivery of salmon calcitonin. Adv Drug Deliv Rev. Aug. 31, 2000;42(3):225-38.*
Tankó et al. Safety and efficacy of a novel salmon calcitonin (sCT) technology-based oral formulation in healthy postmenopausal women: acute and 3-month effects on biomarkers of bone turnover. J Bone Miner Res. Sep. 2004;19(9):1531-8. Epub Jul. 26, 2004.*
U. S. Appl. No. 10/523,421, filed Jul. 31, 2003.*
Buclin et al. Bioavailability and biological efficacy of a new oral formulation of salmon calcitonin in healthy volunteers. J Bone Miner Res. Aug 2002;17(8):1478-85.*
Fortical Nasal Spray for Osteoporosis Launched, from http://goliath.ecnext.com/coms2/gi_0199-4702616/FORTICAL-NASAL-SPRAY-FOR-OSTEOPOROSI, Oct. 1, 2005, pp. 1-3. Accessed May 14, 2009.

* cited by examiner

*Primary Examiner* — David Romeo
(74) *Attorney, Agent, or Firm* — Ann R. Pokalsky, Esq.; Dilworth & Barrese, LLP

(57) ABSTRACT

The invention is directed to a method of administering pharmaceutical compositions comprising peptide drugs such as a calcitonin in combination with one or more oral delivery agents, together with an amount of a liquid, and method of treatment of disorders responsive to the action of peptide drugs such as a calcitonin employing such method of administration so as to enhance the oral bioavailability of a calcitonin. The methods of the invention increase the oral absorption and systemic bioavailability of peptide drugs, such as a calcitonin.

14 Claims, No Drawings

ORAL ADMINISTRATION OF A CALCITONIN

This application is a 371 of PCT/US2008/055399 filed on Feb. 29, 2008, which claims benefit of U.S. provisional Application No. 60/892,594 filed Mar. 2, 2007, which in their entirety are herein incorporated by reference.

BACKGROUND OF THE INVENTION

This invention relates to orally effective pharmaceutical compositions of peptide drugs, the administration thereof, and treatment of disorders responsive to the action of peptide drugs in humans, in particular calcitonin.

Historically, delivery of peptide drugs has been made by injections, because the bioavailability of peptide drugs is too low for these drugs to be administered orally.

SUMMARY OF THE INVENTION

Surprisingly, it has now been found that the oral administration of a peptide drug formulation, e.g. a calcitonin formulation, such as a formulation comprising a calcitonin, and an oral delivery agent for example, sequentially, separately or simultaneously, with a liquid, e.g. a predetermined amount of a liquid, greatly increases the oral absorption and the systemic bioavailability of such a peptide drug, e.g. a calcitonin.

It has also been surprisingly found that the oral administration of a peptide drug formulation, e.g. a calcitonin formulation, such as a formulation comprising a calcitonin, and an oral delivery agent for example, sequentially, separately or simultaneously, with a liquid, e.g. a predetermined amount of a liquid, greatly increases the oral absorption and the systemic bioavailability of such a peptide drug, e.g. a calcitonin when said formulation is administered and/or ingested in the absence of food.

DETAILED DESCRIPTION OF THE INVENTION

The present invention is directed to a pharmaceutical composition which is to be administered together with a liquid, such as water for example.

The present invention is further directed to a pharmaceutical composition which is to be administered together with an amount of liquid, such as water for example, at a certain time interval prior to a meal.

The pharmaceutical composition and its administration is well suited for delivery of peptide drugs, such as a calcitonin.

The present invention is thus directed to a particular method of administering pharmaceutical compositions comprising peptide drugs such as a calcitonin in combination with one or more oral delivery agents, together with an amount of a liquid, and method of treatment of disorders responsive to the action of peptide drugs such as a calcitonin employing such method of administration. Furthermore, the method relates to the timing of administration of the composition.

In one embodiment, the oral administration is made in an amount of liquid, e.g. a small amount, independent of food intake.

In another embodiment, the oral administration according to the present invention is made in the absence of food, advantageously a short interval prior to the consumption of food, for instance, a short interval before a meal, so as to enhance the oral bioavailability of a calcitonin.

The methods of the invention increase the oral absorption and systemic bioavailability of peptide drugs, such as a calcitonin, for example.

In particular, the oral absorption and systemic bioavailability of a peptide drug, e.g. a calcitonin, is increased, e.g. greatly increased, when administered with a liquid, e.g. a small amount of liquid, compared to the administration without a liquid.

In particular, the oral absorption and systemic bioavailability of a peptide drug, e.g. a calcitonin, is increased, e.g. greatly increased, when administered with a liquid prior to a meal, compared to the administration without a liquid prior to a meal.

In particular, the oral absorption and systemic bioavailability of a peptide drug, e.g. a calcitonin, is increased, e.g. greatly increased, when administered with a small amount of liquid prior to a meal, compared to the administration without a larger amount of liquid prior to a meal.

Particularly, the present invention is directed to treatment of disorders responsive to the action of calcitonin, which comprises the oral administration to a human host of a pharmaceutical composition comprising calcitonin and an oral delivery agent, together with an amount of a liquid at a time interval prior to a meal. Disorders responsive to the action of said peptide drugs, such as a calcitonin, for example, are, e.g., Paget's disease, hypercalcemia and osteoporosis.

Calcitonins are commercially available or may be synthesized by known methods. The oral pharmaceutical composition may comprise a therapeutically effective amount of a calcitonin, particularly a calcitonin selected from the group consisting of salmon calcitonin (sCT), (Asu 1-7)-eel calcitonin and human calcitonin, but more particularly a salmon calcitonin in free or salt form.

In one embodiment, the present invention provides a method of oral administration of a pharmaceutical composition comprising a peptide drug to a human host, prior to the consumption of food, in combination with one or more oral delivery agents, wherein the pharmaceutical composition is administered together with an amount of about 5 mL to about 200 mL of a liquid.

In one aspect, the invention provides a method according to the above, wherein the pharmaceutical composition is administered within a range of about 10 minutes to about 120 minutes prior to a meal, but at least 1 hour after the previous meal.

In a further aspect, the invention provides a method according to the above, wherein the liquid is an aqueous liquid.

In a further aspect, the invention provides a method according to the above, wherein the amount of liquid is between about 15 and about 150 mL.

In a further aspect, the invention provides a method according to the above, wherein the amount of water is between about 25 and about 100 mL.

In a further aspect, the invention provides a method according to the above, wherein the amount of water is about 50 mL.

In a further aspect, the invention provides a method according to the above, wherein said pharmaceutical composition comprises:

a) an oral delivery agent being N-(5-chlorosalicyloyl)-8-aminocaprylic acid, N-(10-[2-hydroxybenzoyl]aminodecanoic acid or N-(8-[2-hydroxybenzoyl]amino)caprylic acid, and b) about 0.1-2.5 mg of peptide drug; in which the ratio of the amount of the oral delivery agent, expressed as the corresponding amount of free acid, to the amount of peptide drug is in the range of about 10 to about 250:1 by weight.

In a further aspect, the invention provides a method according to the above, wherein the oral delivery agent is the disodium salt of N-(5-chlorosalicyloyl)-8-aminocaprylic acid, N-(10-[2-hydroxybenzoyl]aminodecanoic acid or N-(8-[2-hydroxybenzoyl]amino)caprylic acid, or a hydrate or solvate of a said disodium salt.

In a further aspect, the invention provides a method according to the above, wherein the peptide drug is a calcitonin.

In a further aspect, the invention provides a method according to the above, wherein the amount of liquid is about 50mL and the time prior to a meal is about 60 minutes and the amount of polypeptide drug is 0.8 mg.

In a further aspect, the invention provides a method according to the above, wherein the amount of liquid is about 50mL and the time prior to a meal is about 60 minutes and the amount of polypeptide drug is 0.6 mg.

In a further aspect, the invention provides a method of treating a disorder responsive to the action of a peptide drug by administering a therapeutic amount of a peptide drug wherein the administration is made by a method according to the above.

In a further aspect, the invention provides a method according to the above, wherein the disorder is osteoporosis and/or osteoarthritis.

In a further aspect, the invention provides a method according to the above for treating osteoarthritis by administering, twice daily, a therapeutic amount of a peptide drug wherein the administration is made by a method according to the above.

In a further aspect, the invention provides a method according to the above, wherein the administration is made once in the morning and once in the evening.

In another embodiment, the invention provides the use of a pharmaceutical composition for the manufacture of a medicament suitable for oral administration, for the treatment of a disorder responsive to the action of peptide drug, said composition comprising a peptide drug in combination with one or more oral delivery agents and wherein said composition is administered orally together with an amount of about 5 ml. to about 200 ml. of a liquid and wherein the pharmaceutical composition is administered within a range of about 10 minutes to about 120 minutes prior to the consumption of food.

In a further aspect, the invention provides the use according to the above, wherein the disorder is osteoporosis or osteoarthritis.

In another embodiment, the invention provides a kit comprising:
a) an oral pharmaceutical composition comprising calcitonin and an oral delivery agent being the disodium salt of N-(5-chlorosalicyloyl)-8-aminocaprylic acid, N-(10-[2-hydroxybenzoyl]aminodecanoic acid or N-(8-[2-hydroxybenzoyl]amino)caprylic acid, or a hydrate or solvate of a said disodium salt; and
b) written instructions to provide said oral pharmaceutical composition to be taken with a liquid in the amount of 5 mL and about 200 mL; or
c) written instructions which instructions provide that said oral pharmaceutical composition may be taken about 2 hours, prior to the consumption of food; and
a liquid in the amount of 5 mL and about 200 mL.

The term "about" as used herein denotes both the actual numbers of values cited, as well as a range falling within up to 10% below and above the cited numbers or values.

The term "small amount" as used herein is between about 5 mL and about 200 mL, for example between about 25mL and about 100mL, such as about 50mL.

The term "calcitonin" as used herein may include natural, synthetic or recombinant human, salmon, pig or eel calcitonin.

The appropriate oral human dosage will vary depending, e.g., on the age of the subject, the oral formulation and the nature and severity of the condition to be treated. An oral human dose of sCT is typically in the range of between 0.4 mg and 2.5 mg, particularly of between 0.6 mg and 1.2 mg, more particularly of between 0.6 mg and 0.8 mg, e.g. 0.6 mg, 0.7 mg, or 0.8 mg, but especially 0.8 mg for a patient, e.g. an average human of about 70 kg.

A useful oral delivery agent is 5-CNAC, particularly the disodium salt or the hydrate or solvate thereof, such as the ethanol solvate.

Typically, the hydrate or ethanol solvate of, e.g., the disodium salt of 5-CNAC contains about one molecule of water or ethanol per molecule of the oral delivery agent, thus being a monohydrate or monoethanol solvate.

As used herein "5-CNAC" denotes N-(5-chlorosalicyloyl)-8-aminocaprylic acid. Unless denoted otherwise, the term "disodium salt" used in connection with 5-CNAC refers to the disodium salt in any form.

5-CNAC is described in U.S. Pat. No. 5,773,647, the contents of which are hereby incorporated by reference, and can be made by methods described therein. The sodium salts and alcohol solvates and hydrates thereof, along with methods for preparing them, are described in WO 00/59863, which is also incorporated herein by reference. Examples 2 and 7 of WO 00/59863 are directed, respectively, to 5-CNAC disodium salt monohydrate and 5-CNAC disodium salt monoethanol solvate.

In a preferred embodiment of the present invention there is provided a method of oral administration of a pharmaceutical composition comprising a peptide drug in combination with one or more oral delivery agents to a human host, and wherein the administration is prior to the consumption of food, wherein the pharmaceutical composition is administered together with an amount of about 5 mL to about 200 mL of a liquid and wherein the pharmaceutical composition is administered within a range of about 10 minutes to about 120 minutes prior to the consumption of food.

The pharmaceutical composition may further comprise a delivery agent, for example 5-CNAC, SNAD and SNAC, and the disodium salts and hydrates and solvates thereof, such as the ethanol solvates. Suitable oral delivery agents are those described in U.S. Pat. Nos. 5,773,647 and 5,866,536, as well as International Application WO 00/59863, the contents of which are incorporated herein by reference. Specific embodiments thereof are The disodium salts, monohydrates and ethanol solvates are described in International Application WO 00/59863, including their preparation.

The liquid is should be a non-toxic liquid, and furthermore be compatible with the peptide drug, so as not to adversely affect the activity of said peptide drug. Therefore, a method according to the above is provided, wherein the liquid is water. A suitable liquid is an aqueous liquid or solution, for example water. The liquid may be any non-toxic liquid which is compatible with the pharmaceutical composition. The liquid may be flavored, and may be any commonly consumed drink.

The amount of liquid, e.g. water may be between about 5 mL and about 200 mL, for example between about 15 mL to about 150 mL, e.g. about 40 mL and about 120 mL, or between about 25 mL and 100 mL, such as about 50 mL.

If the administration is made shortly before a meal, the short interval for administration prior to a meal is at least 10 minutes, and may be up to about 5 hours, e.g. about 2 hours, or about 20 minutes to about 90 minutes, or about 30 to 70 minutes, or about 60 minutes prior to a meal.

The administration is also preferably made at least 30 minutes, preferably at least 1 hour, e.g. at least 4 hours post meal.

A meal may be any standard meal, such as food intake at certain times of the day, e.g. morning (e.g. between about 07.00 and about 08.00), noon (e.g. between about 12.00 and about 13.00) and evening (e.g. between about 18.00 and about 20.00), for example breakfast, lunch and dinner. Preferably, the composition is administered within the above time ranges before the evening meal. For the treatment of osteoarthritis or related diseases, the composition is preferably administered twice daily, preferably within the above time limits, before the morning meal and the evening meal.

A snack may be consumed about 1 hour prior to the pre-evening dosing. In one embodiment, prior to administration according to this invention, no snack is consumed.

In another embodiment, a snack is consumed prior to dosing, for example about 1 hour prior to the pre-evening dosing.

In one embodiment, the invention provides a method of treating osteoarthritis by administering, twice daily, a therapeutic amount of a peptide drug, wherein the administration is made with 50 mL of liquid at least 30 minutes prior to the morning meal and evening meal. A preferred peptide drug is calcitonin.

In one embodiment, the invention provides a method of treating osteoporosis by administering a therapeutic amount of a peptide drug, wherein the administration is made with 50 mL of liquid at least 30 minutes prior to the evening meal. A preferred peptide drug is calcitonin.

Therefore, a particular aspect of the invention is a method of enhancing and maximizing the oral absorption and systemic bioavailability of calcitonin in humans from a formulation comprising a peptide drug, such as calcitonin, and an oral delivery agent by administering said formulation to a human host in need thereof together with an amount of a liquid. The amount of liquid should be as low as possible, while at the same time be enough to enable the patient to swallow the tablet. The amount may, for example, vary between about 5 and about 200 mL. A preferred amount is between about 40 and about 150 mL, or between about 25 mL and about 100 mL. An even more preferred amount is about 50 mL.

In one aspect of the present invention the amount of liquid is between 100 mL and 200 mL and the time prior to a meal is between 15 and 45 minutes, e.g. 30 minutes prior to a meal.

In another aspect of the present invention the amount of liquid is between 5 mL and 100 mL and the time prior to a meal is between 40 and 120 minutes, e.g. 60 minutes prior to a meal.

One beneficial effect of the method according to the invention is that the oral bioavailability is enhanced. In view of the enhanced bioavailability, another aspect of the invention involves a method of reducing the amount of calcitonin required for a therapeutic effect, in a formulation comprising calcitonin and an orally delivery agent to be orally administered to a human host in need thereof, which method comprises the administration of said formulation at a short interval prior to the consumption of food, preferably about 30 minutes to about 1 hour before a meal and preferably as further indicated herein.

The amount of oral delivery agent relative to the amount of calcitonin in the formulations depends on the nature of the delivery agent and is generally in the range of about 10 to about 1,000:1, preferably in the range of about 10 to about 500:1, most preferably about 10 to about 250:1. For example, the ratio by weight of the amount of 5-CNAC disodium salt (expressed as corresponding amount of 5-CNAC free acid) to the amount of sCT is in the range of about 10 to about 250:1, preferably about 25 to about 100:1 when the disodium salt of 5-CNAC is used as an oral delivery agent.

A particular composition for use in the invention may be an oral pharmaceutical composition comprising:
 a) an oral delivery agent being the disodium salt of 5-CNAC, SNAD or SNAC, or a hydrate or solvate of a said disodium salt; and
 b) about 0.1-2.5 mg of calcitonin; in which the ratio of the amount of the oral delivery agent, expressed as the corresponding amount of free acid, to the amount of calcitonin is in the range of about 10 to about 250:1 by weight.

The pharmaceutical composition may comprise 5-CNAC disodium salt or a hydrate thereof and about 0.1-2.5 mg of sCT in which the ratio of the amount of the oral delivery agent to the amount of calcitonin as defined above is in the range of about 10 to about 200:1 by weight, or about 25 to about 100:1 by weight.

A particular aspect of the invention is directed to a kit comprising:
 a) an oral pharmaceutical composition comprising calcitonin and an oral delivery agent being the disodium salt of N-(5-chlorosalicyloyl)-8-aminocaprylic acid, N-(10-[2-hydroxybenzoyl]aminodecanoic acid or N-(8-[2-hydroxybenzoyl]amino)caprylic acid, or a hydrate or solvate of a said disodium salt; and
 b) written instructions to provide said oral pharmaceutical composition to be taken with a liquid in the amount of 5 and about 200 mL, preferably between about 40 and about 150 mL, or even more preferred about 50 mL; or
 c) written instructions which instructions provide that said oral pharmaceutical composition may be taken about 2 hours, advantageously about 20 minutes to about 70 minutes, preferably about 30 to 70 minutes, or most preferably about 60 minutes prior to the consumption of food; and
 a liquid in the amount of 5 mL and about 200 mL, preferably between about 40 mL and about 150 mL, between 25 mL and 100 mL, or even more preferred about 50 mL.

The kit may comprise next to the written instructions as mentioned above, about 0.1-2.5 mg of calcitonin; in which the ratio of the amount of the oral delivery agent, expressed as the corresponding amount of free acid, to the amount of calcitonin is in the range of about 10 to about 250:1 by weight. More preferred is a kit comprising 5-CNAC disodium salt or a hydrate thereof and about 0.1-2.5 mg of sCT in which the ratio of the amount of the oral delivery agent to the amount of calcitonin as defined above is in the range of about 10 to about 200:1 by weight.

The solid pharmaceutical compositions used for oral administration may be in form of a capsule (including a soft-gel capsule), tablet, caplet or other solid oral dosage form, all of which can be prepared by methods well-known in the art.

Preferably, the solid pharmaceutical compositions also contain a crospovidone and/or povidone, advantageously crospovidone.

The crospovidone can be any crospovidone. Crospovidone is a synthetic cross-linked homopolymer of N-vinyl-2-pyrrolidone, also called 1-ethenyl-2-pyrrolidinone, having a molecular weight of 1,000,000 or more. Commercially available crospovidones include Polyplasdone XL, Polyplasdone XL-10, Polyplasdone INF-10 available from ISP, Kollidon CL, available from BASF Corporation. The preferred crospovidone is Polyplasdone XL.

Povidone is a synthetic polymer consisting of linear 1-vinyl-2-pyrrolidinone groups having a molecular weight generally between 2,500 and 3,000,000. Commercially available povidones include Kollidon K-30, Kollidon K-90F available from BASF Corporation and Plasdone K-30 and Plasdone K-29/32, available from ISP.

The crospovidones and povidones are commercially available. Alternatively, they may be synthesized by known processes.

The crospovidone, povidone or combination thereof is generally present in the compositions in an amount of from 0.5-50% by weight relative to the total weight of the overall pharmaceutical composition, preferably an amount of from 2-25%, more preferably 5-20% by weight relative to the total weight of the pharmaceutical composition.

A particular aspect of the invention is a pharmaceutical composition for oral administration of sCT to humans which comprises 5-CNAC disodium salt, calcitonin and crospovidone, the weight ratio of 5-CNAC as free acid to sCT being in the range of about 10 to about 200:1.

Alternatively, the solid pharmaceutical compositions may contain croscarmellose sodium (AC-DI-SOL®) and/or colloidal silicon dioxide (CAB-O-SIL®).

Also, the calcitonin and oral delivery agent may be used in the form of a colyophilized mixture, e.g., of sCT and the disodium salt of 5-CNAC.

The compositions may additionally comprise additives in amounts customarily employed including, but not limited to, a pH adjuster, a preservative, a flavorant, a taste-masking agent, a fragrance, a humectant, a tonicifier, a colorant, a surfactant, a plasticizer, a lubricant, such as magnesium stearate, a flow aid, a compression aid, a solubilizer, an excipient, a diluent, such as microcrystalline cellulose, e.g., Avicel PH 102 supplied by FMC Corporation, or any combination thereof. Other additives may include phosphate buffer salts, citric acid, glycols and other dispersing agents.

The compositions are administered orally, typically once a day, for instance, before an evening meal, to systemically deliver a therapeutically effective amount of calcitonin, if the composition is intended for the treatment of osteoporosis.

The compositions are administered orally, typically twice per day, for instance, before a morning meal and an evening meal, to systemically deliver a therapeutically effective amount of calcitonin, if the composition is intended for the treatment of osteoarthritis.

If the pharmaceutical composition is intended to be used for the treatment of osteoporosis, the composition should preferably be taken with an amount of water of about 50 to about 100 mL of liquid, at about 30 to about 60 minutes before the evening meal.

If the pharmaceutical composition is intended to be used for the treatment of osteoarthritis, the composition should preferably be taken with an amount of water of about 50 to about 100 mL of liquid, twice daily at about 30 to about 60 minutes before the morning meal and the evening meal.

The solid pharmaceutical compositions of the instant invention can be prepared by conventional methods, e.g., by blending a mixture of the active agent or active agents, the delivery agent and other ingredients, and filling into capsules or, instead of filling into capsules, compression-molding to give tablets. In addition, a solid dispersion may be formed by known methods followed by further processing to form a tablet or capsule.

Typical pharmaceutical formulations are given in the examples. In the examples, 5-CNAC denotes N-(5-chlorosalicyloyl)-8-aminocaprylic acid. When its disodium salt is an ingredient in the examples, a corresponding amount of the disodium salt monohydrate is actually used. The amount given in the examples is the amount of the anhydrous disodium salt.

The increase in oral absorption and systemic bioavailability of calcitonin is determined by measuring the plasma concentration of calcitonin achieved after administration of the drug together with varying amounts of water and at various intervals prior to a meal and at mealtime. Typically, the plasma concentration is measured at predetermined periods after the administration of the drug so as to determine the maximum plasma concentration ($C_{max}$) and the total amount absorbed as determined by the area under the curve (AUC).

EXAMPLES

Compositions of the present invention may be made according to the following examples.

Example 1

Tablet Formulation 0.52 g of sCT, pre-screened through a 40-mesh screen, 120 g of 5-CNAC disodium salt, pre-screened through a 35-mesh screen, and 20 g of Polyplasdone XL (crospovidone, NF) is combined in a 500 mL jar and is mixed using a Turbula mixer for 2 minutes at a speed of 46 RPM. An additional 125.4 g of 5-CNAC disodium salt, pre-screened through a 35-mesh screen, and 32.5 g of Avicel PH 102 is added to the jar and is mixed for a period of 8 minutes at a speed of 46 RPM. A further 32.5 g of Avicel is added to the jar and is mixed for 5 minutes at a speed of 46 RPM. 4.0 g of magnesium stearate is screened into the jar using a 35-mesh screen and is blended for 1 minute at a speed of 46 RPM. The final blend is compressed into tablets using a Manesty B3B tablet press. The tablet weight is approximately 400 mg.

Example 2

Tablet formulation

A mixture of 14 g of the disodium salt of 5-CNAC and 0.56 g of CAB-O-SIL is sieved through a 40-mesh screen. 0.3 g of the 5-CNAC disodium/CAB-O-SIL mixture, 0.028 g sCT, pre-screened through a 40-mesh screen, and 0.56 g of AC-DI-SOL, pre-screened through a 30-mesh screen are combined in a 1 quart V-blender shell. The mixture is blended for two minutes. Approximately 14.3 g of the 5-CNAC disodium/CAB-O-SIL mixture is added geometrically to the V-blender shell and mixed for 2 minutes after each addition (approximately 0.8, 1.7, 3.2 and 8.6 g are added successively). 12.43 g of Avicel PH 102 and 0.42 g of magnesium stearate, pre-screened through a 40-mesh screen are added to the V-blender shell and mixed for 5 minutes. The final blend is then screened through a 40-mesh screen and is compressed into tablets using, e.g., a Manesty F3 press. The tablet weights are approximately 400 mg.

Example 3

Tablet formulation 0.1224 of sCT, pre-screened through a 40-mesh screen, 30 g of 5-CNAC disodium salt, pre-screened through a 35-mesh screen, and 4 g of AC-DI-SOL are placed in a 500 mL Pyrex® jar and are mixed using a Turbula mixer for 2 minutes at a speed of 46 RPM. An additional 31.35 g of 5-CNAC disodium salt, pre-screened through a 35-mesh screen, and 15 g of Avicel PH 102 are added to the jar and are mixed for a period of 8 minutes at a speed of 46 RPM. 2 g of CAB-O-SIL and 16.15 g of Avicel are combined and are screened through an 18-mesh screen. The CAB-O-SIL/Avicel mixture is added to the jar and is mixed for 5 minutes at a speed of 46 RPM. 1.5 g of magnesium stearate is screened into the jar using a 35-mesh screen and is blended for 2 minutes at a speed of 46 RPM. The final blend is compressed into tablets using a Manesty B3B tablet press. The tablet weights are approximately 400 mg.

Example 4

Capsule Formulation 18 kg of water for injection and 0.16 kg of sodium hydroxide, NF, are added to a vessel and mixed until dissolved. 0.800 kg of the free acid of 5-CNAC is added to the vessel and stirred at 400-600 RPM for a minimum of 10 minutes. The pH of the vessel is adjusted to approximately 8.5 using 10 N sodium hydroxide. The vessel is stirred for a minimum of 10 minutes after each addition of 10 N sodium hydroxide. The 10 N sodium hydroxide is prepared by adding 40 g of sodium hydroxide, NF, to 100 mL of water for injection. The final weight of the compounded solution is adjusted to 20.320 kg by the addition water for injection (density 1.016). The vessel is stirred at 400-600 RPM for a minimum of 30 minutes. The compounded solution is filtered into another vessel using a peristaltic pump, silicone tubing, and a DuraPore 0.45 µm MPHL membrane capsule filter. A phosphate buffer solution is prepared by adding 13.8 g of monosodium phosphate monohydrate, USP to 900 g of water for injection and adjusting to a pH of 4.0 utilizing a 1.0 N phosphoric acid solution. The phosphoric acid solution is prepared by adding 0.96 g of phosphoric acid, NF, to 25 mL of water for injection. The final weight of the phosphate buffer solution is adjusted to 1007 g (density 1.007) using water for injection and is stirred for 5 minutes.

A buffered sCT solution is prepared by adding 1.6 g of sCT to 660 g of the phosphate buffer solution. The final weight of the solution is adjusted to a final weight of 806.4 g (density 1.008) using the phosphate buffer solution and mixed for a minimum of 5 minutes at a speed of 250 RPM or less.

0.800 kg of the buffered sCT solution is added dropwise to 20 kg of 5-CNAC solution with constant mixing at a speed of 250 RPM or less for a minimum of 5 minutes. Approximately 0.75 L of the sCT/5-CNAC solution is filled into stainless steel lyophilization trays (30.5×30.5 cm) for a final solution depth of 0.8-0.9 cm. Approximately 29 trays are filled with 21.75 L of sCT/5-CNAC solution. The trays are placed into an Edwards freeze dryer and lyophilized according to the following procedure:

1. When trays are loaded and the Reeze dryer is sealed, the shelves are cooled at a rate of 1° C. per minute.
2. Once the shelf temperature reaches −45° C., the shelf temperature is maintained at −45° C. for a minimum of 120 minutes.
3. The condenser is cooled to −50° C. or below.
4. The chamber is evacuated and when a vacuum of 300 microns is maintained, the shelf temperature is raised to −30° C. at a rate of 1° C. per minute.
5. The shelf temperature is maintained at −30° C. for 180 minutes.
6. The pressure in the chamber is reduced to 200 microns and when a vacuum of 200 microns is maintained, the shelf temperature is raised to −20° C. at a rate of 1° C. per minute.
7. The shelf temperature is maintained at −20° C. for 200 minutes.
8. The shelf temperature is raised to −10° C. at a rate of 1° C. per minute.
9. The shelf temperature is maintained at −10° C. for 360 minutes.
10. The shelf temperature is raised to 0° C. at a rate of 1° C. per minute.
11. The shelf temperature is maintained at 0° C. for 720 minutes.
12. The pressure in the chamber is reduced to 100 microns and when a vacuum of 100 microns is maintained, the shelf temperature is raised to +10° C. at a rate of 1° C. per minute.
13. The shelf temperature is maintained at +10° C. for 540 minutes.
14. The shelf temperature is raised to +25° C. at a rate of 1° C. per minute.
15. The shelf temperature is maintained at +25° C. for 440 minutes.
16. The vacuum is released and trays are unloaded.

The colyophilized sCT/5-CNAC is removed from the trays and stored in polyethylene and foil bags under refrigeration. Approximately 400 mg of colyophilized material is filled into capsules (size M) for administration.

Example 5

Tablet Formulation

The following tablet formulations are prepared similarly to Example 1.

|  | Amount of sCT per tablet | | | |
|---|---|---|---|---|
| Ingredients | 0.15 mg | 0.4 mg | 1 mg | 2.5 mg |
| Salmon calcitonin | 0.15 mg | 0.4 mg | 1 mg | 2.5 mg |
| 5-CNAC disodium salt* | 228 mg | 228 mg | 228 mg | 228 mg |
| Microcrystalline cellulose, NF (Avicel PH-102) | 147.85 mg | 147.6 mg | 147 mg | 145.5 mg |
| Crospovidone, NF | 20 mg | 20 mg | 20 mg | 20 mg |
| Magnesium stearate, NF | 4 mg | 4 mg | 4 mg | 4 mg |
| Total | 400 mg | 400 mg | 400 mg | 400 mg |

*The material used is 5-CNAC disodium salt monohydrate in an amount corresponding to 228 mg of anhydrous 5-CNAC disodium salt, which amount is equivalent to 200 mg of 5-CNAC free acid.

An additional formulation is prepared according to:

| Ingredients | Composition per unit [%] | Composition per unit [mg/unit] |
|---|---|---|
| Calcitonin | 0.16 | 0.8 |
| 5-CNAC disodium salt | 45.6 | 228.0 |
| Cellulose Microcrystalline, powder | 48.94 | 244.7 |
| Crospovidone | 5.0 | 25.0 |
| Aerosil 200 PH | 0.3 | 1.5 |

Example 6

Tablet Formulation

Similarly prepared to Example 1 are tablets containing 0.5 or 1 mg of sCT and 5-CNAC disodium salt in an amount corresponding to 25, 50, 100, 200 and 400 mg of 5-CNAC free acid.

Example 7

Clinical Data, Experimental Setup

The effect of administration of a tablet formulation of sCT in combination with 5-CNAC with various amounts of water at various time intervals relative to meals is measured in human subjects.

A cross-over study to investigate the food effect and water intake on PK and PD profile of calcitonin 0.8 mg was performed, wherein calcitonin 0.8 mg given with 50 mL or 200 mL water intake, at a dosing time of 10 min, 30 min or 60 min before a meal. A matching placebo was given with 200 mL water, at a dosing time 10 min, 30 min or 60 min before a meal. The population used in the study was 56 healthy postmenopausal women, 40-70 years of age.

A partially blinded, randomized, single-dose, placebo controlled cross-over study was performed. Each subject was randomized to one of 56 pre-defined sequences, wherein each sequence included 5 treatments from the list below. A minimum of 3 days wash-out was done between each period. The results are shown in tables IV and V.

TABLE III

Treatment schedule

| Treatment | Study medication | Water intake volume | Pre-meal dosing time |
|---|---|---|---|
| 1. | calcitonin 0.8 mg | 50 mL | 10 mins |
| 2. | calcitonin 0.8 mg | 50 mL | 30 mins |
| 3. | calcitonin 0.8 mg | 50 mL | 60 mins |
| 4. | calcitonin 0.8 mg | 200 mL | 10 mins |
| 5. | calcitonin 0.8 mg | 200 mL | 30 mins |
| 6. | calcitonin 0.8 mg | 200 mL | 60 mins |
| 7. | Placebo | 200 mL | 10 mins |
| 8. | Placebo | 200 mL | 30 mins |
| 9. | Placebo | 200 mL | 60 mins |
| 10. | Miacalcic 200 IU | N/A | 60 mins |

Demographic summary of the subjects:

| | All sequences (N = 56) |
|---|---|
| Age (years) Mean (SD) | 64.2 (3.50) |
| Race: Caucasian (%) | 56 (100.0%) |
| Height (cm) Mean (SD) | 163.9 (5.91) |
| Weight (kg) Mean (SD) | 68.50 (7.84) |
| CTX-I (ug/L) pre-dose at first period, Mean (SD) | 0.672 (0.229) |

Example 8

Biological Data, Results

Geometric mean estimates for sCT $C_{max}$ and $AUC_{0-4}$ on day 1 of the six calcitonin—water volume—pre-meal dosing time combinations were calculated, including 95% confidence intervals. Geometric means ratios (test/reference) and 95% confidence intervals were also calculated for 0.8 mg oral dose of a calcitonin tablet.

TABLE IV

| | Calcitonin absorption | |
|---|---|---|
| Treatment Group | AUC(0-4)(pg · h/mL) Geometric means | Cmax (pg/mL) Geometric means |
| Calcitonin, 200 mL, 10 min pre-meal | 18.06 | 51.50 |
| Calcitonin, 200 mL, 30 min pre-meal | 23.87 | 57.22 |
| Calcitonin, 200 mL, 60 min pre-meal | 20.84 | 49.45 |
| Calcitonin, 50 mL, 10 min pre-meal | 41.13 | 100.10 |
| Calcitonin, 50 mL, 30 min pre-meal | 59.28 | 123.90 |
| Calcitonin, 50 mL, 60 min pre-meal | 67.84 | 152.77 |

These results show that oral administration of a tablet of calcitonin together with an amount of 50 mL water gives a two to three times higher $C_{max}$ than with an amount of 200 mL.

Example 9

Pharmacodynamics

Serum CTX-I, or CrossLaps® (Nordic Bioscience Diagnostics A/S, cat. no. 4CRL4000) is an enzyme-immunoassay for quantitative assessment of bone resorption, and has been cleared by the FDA. It is based on two highly specific monoclonal antibodies against the amino acid sequence of EKAHD-β-GGR originating from the C-telopeptide of type I collagen. The aspartic acid residue (D) is β-isomerized. Standards, control, or unknown serum samples are pipetted into the appropriate microtitre wells coated with streptavidin, followed by application of a mixture of a biotinylated antibody and a peroxidase-conjugated antibody. Then, a complex between the CTX antigens, biotinylated antibody and peroxidase-conjugated antibody is generated, and this complex binds to the streptavidin surface via the biotinylated antibody. Following the one-step incubation at room temperature, the wells are emptied and washed. A chromogenic substrate is added and the colour reaction is stopped with sulfuric acid. Finally, the absorbance is measured.

The pharmacodynamic (PD) profile on the serum biomarker CTX-I (evaluated by the nadir and $AOC_{0-6}$) of 0.8 mg SMCO21 combined with the water intake volume (50 or 200 mL) and pre-meal dosing time (10, 30 or 60 min) compared to placebo with matching pre-meal dosing time and 200 mL water intake volume. Serum CTX-I is a collagen telopeptide epitope and is a marker of bone resorption. Concentration of CTx in serum was estimated by ELISA (Serum Cross-Laps One Step ELISA; Osteometer Biotech, Herlev, Denmark).

TABLE V

| Nadir % change from baseline (90% CI) |
|---|
| 50 mL water, SMC021 (SMC) |
| 10 min pre-meal: −79.9 (−81.9, −78.0) |
| 30 min pre-meal: −82.6 (−84.6, −80.7) |
| 60 min pre-meal: −83.4 (−85.3, −81.4) |
| 200 mL water, SMC021 (SMC) |
| 10 min pre-meal: −75.3 (−77.2, −73.3) |
| 30 min pre-meal: −77.1 (−79.1, −75.2) |

TABLE V-continued

Nadir % change from baseline (90% CI)

60 min pre-meal: −77.2 (−79.1, −75.3)
200 mL water, Placebo (PBO)

10 min pre-meal: −57.6 (−61.2, −54.0)
30 min pre-meal: −59.4 (−63.1, −55.8)
60 min pre-meal: −56.9 (−60.6, −53.3)

These results show that administration of an oral table of SMCO21 together with an amount of 50 mL water reduces CTX-I to a lower nadir than with an amount of 200 mL.

The invention claimed is:

1. A method of oral administration of a pharmaceutical composition, comprising a calcitonin, to a human host, prior to the consumption of food, in combination with one or more oral delivery agents, selected from the group consisting of N-(5-chlorosalicyloyl) -8-aminocaprylic acid (5-CNAC), N-(10-[2-hydroxybenzoyl]aminodecanoic acid (SNAD) or N-8-[2-hydroxybenzoyl]amino) caprylic acid (SNAC), and the disodium salts and hydrates and solvates thereof, wherein the pharmaceutical composition is administered together with an amount of about 25 mL to about 100 mL of a liquid.

2. The method according to claim 1, wherein the pharmaceutical composition is administered within a range of about 10 minutes to about 120 minutes prior to a meal, and at least 1 hour after the previous meal.

3. The method according to claim 1, wherein the liquid is an aqueous liquid.

4. The method according to claim 1, wherein the amount of liquid is about 50 mL.

5. The method according to claim 1, wherein said pharmaceutical composition comprises:
   a) an oral delivery agent being 5-CNAC, SNAD or SNAC or a disodium salt, hydrate, or solvate thereof, and
   b) from about 0.4 to about 2.5 mg of calcitonin; in which the ratio of the amount of the oral delivery agent, expressed as the corresponding amount of free acid, to the amount of calcitonin is in the range of about 10 to about 250:1 by weight.

6. The method according to claim 5, wherein the oral delivery agent is the disodium salt of 5-CNAC or a hydrate or solvate of a said disodium salt.

7. The method according to claim 2, wherein the composition is administered about 60 minutes prior to the meal.

8. A method of treating osteoporosis by administering a therapeutic amount of a calcitonin wherein the administration is made by the method of claim 1.

9. A method of treating osteoarthritis by administering, twice daily, a therapeutic amount of a calcitonin wherein the administration is made by the method of claim 1.

10. The method according to claim 9, wherein the administration is made once in the morning and once in the evening.

11. A method of treating osteoarthritis by administering, twice daily, a therapeutic amount of a calcitonin together with one or more oral delivery agents selected from the group consisting of 5-CNAC, SNAD, SNAC, and the disodium salts and hydrates and solvates thereof, wherein the administration is made with about 50mL of liquid at least 30 minutes prior to the morning meal and evening meal.

12. The method of claim 5 wherein the amount of calcitonin is from about 0.6 to about 1.2 mg.

13. The method of claim 11, wherein the administration is made twice daily, once in the morning and once in the evening.

14. A method of treating osteoporosis by administering a therapeutic amount of a calcitonin together with one or more oral delivery agents selected from the group consisting of 5-CNAC, SNAD, SNAC, and the disodium salts and hydrates and solvates thereof, wherein the administration is made with about 50mL of liquid at least 30 minutes prior to the evening meal.

* * * * *